(12) United States Patent
Yamamoto

(10) Patent No.: US 8,432,161 B2
(45) Date of Patent: Apr. 30, 2013

(54) FREQUENCY SELECTION METHOD AND HARDENING DEPTH MEASUREMENT METHOD OF EDDY CURRENT MEASUREMENT

(75) Inventor: Takanari Yamamoto, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 238 days.

(21) Appl. No.: 12/810,875

(22) PCT Filed: Oct. 16, 2009

(86) PCT No.: PCT/JP2009/005407
§ 371 (c)(1),
(2), (4) Date: Jun. 28, 2010

(87) PCT Pub. No.: WO2010/050134
PCT Pub. Date: May 6, 2010

(65) Prior Publication Data
US 2012/0126802 A1 May 24, 2012

(30) Foreign Application Priority Data
Oct. 28, 2008 (JP) ................................. 2008-276575

(51) Int. Cl.
*G01N 27/275* (2011.01)
(52) U.S. Cl.
USPC .......................................................... 324/239
(58) Field of Classification Search .......................... None
See application file for complete search history.

(56) References Cited

U.S. PATENT DOCUMENTS 5,648,611 A * 7/1997 Singh et al. ..................... 73/598

FOREIGN PATENT DOCUMENTS

| JP | A-2002-14081 | 1/2002 |
| JP | A-2004-108573 | 4/2004 |
| JP | A-2008-157907 | 7/2008 |
| JP | A-2008-170233 | 7/2008 |
| JP | A-2009-31112 | 2/2009 |
| WO | WO 2008/126554 A1 | 10/2008 |

OTHER PUBLICATIONS

International Search Report issued in International Application No. PCT/JP2009/005407 on Jan. 12, 2010 (with translation).

* cited by examiner

*Primary Examiner* — Paresh Patel
(74) *Attorney, Agent, or Firm* — Oliff & Berridge, PLC

(57) ABSTRACT

Disclosed is a method of appropriately and easily selecting a combination of two different frequencies of an AC exciting signal used for eddy current measurement while decreasing or removing the dependence of the measurement accuracy on temperature. Three or more AC exciting signals of different frequencies are applied to an object under measurement by an exciting coil, and an induced current is produced. Detection signals corresponding to the frequencies are detected by a detection coil, and the phase difference between each detection signal and the AC exciting signal corresponding to each frequency is calculated from the detection signals corresponding to the frequencies. From the phase differences, a combination of two frequencies the phase differences of which are within a predetermined range is extracted. The lower frequency of the extracted combination is used for a first frequency, and the higher one is used as a second frequency. Thus, the combination of two frequencies are selected.

3 Claims, 9 Drawing Sheets

FREQUENCY SELECTION METHOD AND HARDENING DEPTH MEASUREMENT METHOD OF EDDY CURRENT MEASUREMENT

TECHNICAL FIELD

The present invention relates to an art for measuring a measurement object noncontactly (nondestructively) with eddy current, for example, measuring depth of a hardening layer formed on a surface of a member of a steel material by hardening process (hardening depth).

In more detail, the present invention relates to an art for selecting appropriately frequency of induced current for generating the eddy current.

BACKGROUND ART

Conventionally, as a method for measuring depth of a hardening layer formed on a surface of a member of a steel material by hardening process (hardening depth), there is known a method that a part of members hardened at the same batch is cut and texture observation of the cut surface is performed or distribution of Vickers hardness in the depth direction of the cut surface is measured.

However, the method has various problems such as shown below. (1) The process of cutting a part of members which is possible to be a product is included so that the cut measurement object must be scraped, whereby yield of the productions is reduced. (2) A series of processes such as cutting, processing of the cut surface (grinding, etching and the like), observing of the cut surface with an electron microscope or measuring hardness with a Vickers hardness testing machine so that time required for the measurement is long. (3) According to the above-mentioned reasons, the method is not applicable to total inspection. (4) The total quality assurance by the sampling inspection has a limit, and according to the measurement result of the measurement object, all the members hardened at the same batch must be treated as nonconforming articles, whereby yield of the productions is also reduced.

For solving such the problems, noncontact measurement of the hardening depth with a so-called eddy current sensor is examined. Examples thereof are described in the Patent Literatures 1 and 2.

In the method described in the Patent Literature 1, a magnetization coil of the eddy current sensor inserted thereto with a measurement object generates an alternating current magnetic field, eddy current is generated on the surface of the measurement object by the alternating current magnetic field, magnitude of an induced magnetic field generated by the eddy current is detected as output voltage with a detection coil of the eddy current sensor inserted thereto with the measurement object, and the relation between hardening depth of a known measurement object of the same material with output voltage is compared with the output voltage of the detection coil so as to measure depth of a hardening layer.

In the method described in the Patent Literature 2, alternating current voltage (alternating current magnetization signal) of a plurality of different frequencies is applied on a magnetization coil of the eddy current sensor inserted thereto with a measurement object, eddy current is generated on the surface of the measurement object by the magnetization coil, magnitude of an induced magnetic field generated by the eddy current is detected as output voltage (detection signal) with a detection coil of the eddy current sensor inserted thereto with the measurement object, distribution of hardness in the depth direction of the measurement object is measured based on amplitude ratio of the alternating current magnetization signal and the detection signal, and hardening depth of the measurement object is measured based on phase difference of the detection signal about the alternating current magnetization signal.

According to the method described in the Patent Literature 2, the distribution of hardness in the depth direction and the hardening depth of the measurement object can be measured noncontactly simultaneously, and the method is applicable to the total inspection.

However, the methods described in the Patent Literatures 1 and 2 have a problem that, when the temperature of the measurement object at the time of measurement is changed by rot change of the measurement object or change of measurement environment, the measurement result of the hardening depth is changed, whereby accurate measurement of the hardening depth is difficult.

That is because the change of the temperature of the measurement object causes change of permeability and conductivity of the measurement object, whereby the output voltage (detection signal) of the detection coil is changed.

In the case that the measurement object is a drive shaft made by a steel material hardened with high frequency, environment temperature of a production factory of the drive shaft is changed for about 30° C. between the daytime of midsummer (about 35° C.) and the early morning of midwinter (about 5° C.), and the temperature is changed widely between the daytime and nighttime of the same day.

Since the temperature of the drive shaft is higher than the environment temperature, in the case that the time from the hardening to the start of measurement of the hardening depth is different from that at ordinary times, for example the case that the production factory stopped temporary is restarted, the temperature of the drive shaft at the time of measurement of the hardening depth is changed.

As a method for preventing the reduction of measurement accuracy of the hardening depth caused by such temperature change, below methods are supposable. (1) The measurement is performed while temperature of the measurement object, the measurement device and the environment around them is kept constantly by air conditioning equipment. (2) The temperature of the measurement object is measured just before the measurement of the hardening depth and the measurement result of the hardening depth is corrected based on the measured temperature.

However, in the method (1), the cost of equipment is large, and the measurement cannot be performed until the temperature of the measurement object, the measurement device and the environment around them are kept constantly (the working efficiency is not good).

In the method (2), the temperature measurement of the measurement object is performed in addition to the measurement of the hardening depth so that the number of the processes is increased. Especially, since the temperature measurement is difficult to be performed for short time generally (the object must be kept until the measurement temperature reaches equilibrium condition), time for the measurement of the hardening depth of one measurement object is long, whereby it is difficult to apply the method to the total inspection in the production process of the measurement object.

For solving the above problems, the inventor has obtained below knowledge. The alternating current magnetization signals of two different frequencies are applied on a drive shaft with a magnetization coil so that induced currents of eddy currents respectively corresponding to the two different frequencies are generated in the drive shaft. Detection signals caused by the induced currents corresponding to the two different frequencies are detected with a detection coil. Based on amplitude of the detection signal corresponding to one of the two different frequencies, phase difference between the alternating current magnetization signal and the detection signal corresponding to one of the two different frequencies, amplitude of the detection signal corresponding to the other of the two different frequencies, and phase difference between the alternating current magnetization signal and the detection signal corresponding to the other of the two different frequencies, difference D shown in below formula 1 is calculated. The hardening depth of the drive shaft is measured based on the difference D. According to the method of performing the above-mentioned series of works, the hardening depth of the drive shaft can be measured noncontactly (non-destructively) quickly regardless of the change of the environment temperature and the temperature of the drive shaft itself, whereby the method is applicable to the total inspection of the measurement object (in-line inspection).

$$D = \frac{\sqrt{X_1^2 + Y_1^2} - \sqrt{X_2^2 + Y_2^2}}{\sqrt{X_2^2 + Y_2^2}} \qquad \text{[Formula 1]}$$

However, the above method has below problems.

For securing enough measurement accuracy in the method, it is necessary to select appropriately the combination of two different frequencies of the alternating current magnetization signals applied on the drive shaft. However, the combination of two different frequencies must be selected by trial and error (concretely, detection signals are obtained while the combination of frequencies is changed variously about a plurality of measurement portions of the measurement object, and based on the measurement, the result of calculation of hardening depth is compared with hardening depth actually obtained by cutting the measurement portion and inspecting with a microscope or measuring Vickers hardness), whereby much manpower and time is required for selecting the appropriate combination of two frequencies.

Since the appropriate combination of two frequencies is changed following the change of shape or measurement portion of the measurement object, the work for selecting the appropriate combination of two frequencies must be performed for every measurement object or every measurement portion.

The cause of the trial and error in the selection of the combination of frequencies is decrease of measurement accuracy following change of the environment temperature and the temperature of the measurement object. Then, the method for selecting the combination of frequencies is desirable that the mechanism of temperature dependency of the measurement accuracy is elucidated and the temperature dependency of the measurement accuracy is reduced or eliminated efficiently in accordance with a fixed rule.

[Patent Literature 1] JP 2002-14081 A
[Patent Literature 2] JP 2004-108873 A

DISCLOSURE OF INVENTION

Problems to be Solved by the Invention

The present invention is provided in view of the above-mentioned situation so as to provide a method for selecting frequency at eddy current measurement that combination of two different frequencies of alternating current magnetization signals used in the eddy current measurement can be selected appropriately and easily while the temperature dependency of the measurement accuracy is reduced or eliminated.

Means of Solving the Problems

The above-mentioned problems are solved by the following means.

The first aspect of the present invention is a frequency selection method of eddy current measurement, wherein a magnetization coil applies alternating current magnetization signals of a first frequency and a second frequency different from the first frequency on an measurement object so as to generate induced currents including eddy currents respectively corresponding to the first frequency and the second frequency in the measurement object, a detection coil detects detection signals caused by the induced currents respectively corresponding to the first frequency and the second frequency, a phase difference D shown in below formula 1 is calculated based on an amplitude Y1 of the detection signal corresponding to the first frequency, a phase difference X1 of the alternating current magnetization signal and the detection signal corresponding to the first frequency, an amplitude Y2 of the detection signal corresponding to the second frequency, and a phase difference X2 between the alternating current magnetization signal and the detection signal corresponding to the second frequency, and the measurement object (the hardening depth thereof) is measured based on the phase difference D. The frequency selection method includes: a results of the magnetization and detection process for frequency selection that the magnetization coil applies alternating current magnetization signals of three or more different frequencies on the measurement object so as to generate induced currents respectively corresponding to the three or more different frequencies in the measurement object and the detection coil detects the detection signals caused by the induced currents respectively corresponding to the three or more different frequencies; a phase difference calculation process that phase differences between the alternating current magnetization signals and the detection signals respectively corresponding to the three or more different frequencies are calculated based on the detection signals caused by the induced currents respectively corresponding to the three or more different frequencies detected in the magnetization and detection process for frequency selection; and a frequency sampling process that a combination of two frequencies which make a difference of the phase differences within a predetermined range is extracted from the three or more different frequencies calculated in the phase difference calculation process, and lower one of the two frequencies of the combination is referred to as the first frequency and higher one thereof is referred to as the second frequency.

$$D = \frac{\sqrt{X_1^2 + Y_1^2} - \sqrt{X_2^2 + Y_2^2}}{\sqrt{X_2^2 + Y_2^2}} \qquad \text{[Formula 1]}$$

In the frequency selection method according to the present invention, preferably, the phase difference D is substituted for a relational expression of the difference D, a hardening depth H of the measurement object, and constants A and B shown in below formula 2 so as to calculate the hardening depth H of the measurement object.

$$D = A \times H^3 + B \qquad \text{[Formula 2]}$$

The second aspect of the present invention is a hardening depth measurement method: including a magnetization and detection process that a magnetization coil applies alternating current magnetization signals of a first frequency and a second frequency different from the first frequency on a measurement object so as to generate induced currents including eddy currents respectively corresponding to the first frequency and the second frequency in the measurement object, and a detection coil detects detection signals caused by the induced currents respectively corresponding to the first frequency and the second frequency; a difference calculation process that a phase difference D shown in below formula 1 is calculated based on an amplitude Y1 of the detection signal corresponding to the first frequency, a phase difference X1 of the alternating current magnetization signal and the detection signal corresponding to the first frequency, an amplitude Y2 of the detection signal corresponding to the second frequency, and a phase difference X2 between the alternating current magnetization signal and the detection signal corresponding to the second frequency; and a hardening depth calculation process that the difference D calculated in the difference calculation process is substituted for a relational expression of the difference D, a hardening depth H of the measurement object, and constants A and B shown in below formula 2 so as to calculate the hardening depth H of the measurement object.

Effect of the Invention

According to the frequency selection method which is the first aspect of the present invention, combination of two different frequencies of alternating current magnetization signals used in the eddy current measurement can be selected appropriately and easily while the temperature dependency of the measurement accuracy is reduced or eliminated.

According to the hardening depth measurement method which is the second aspect of the present invention, the hardening depth of the measurement object can be measured noncontactly accurately.

THE BEST MODE FOR CARRYING OUT THE INVENTION

Figure 1:
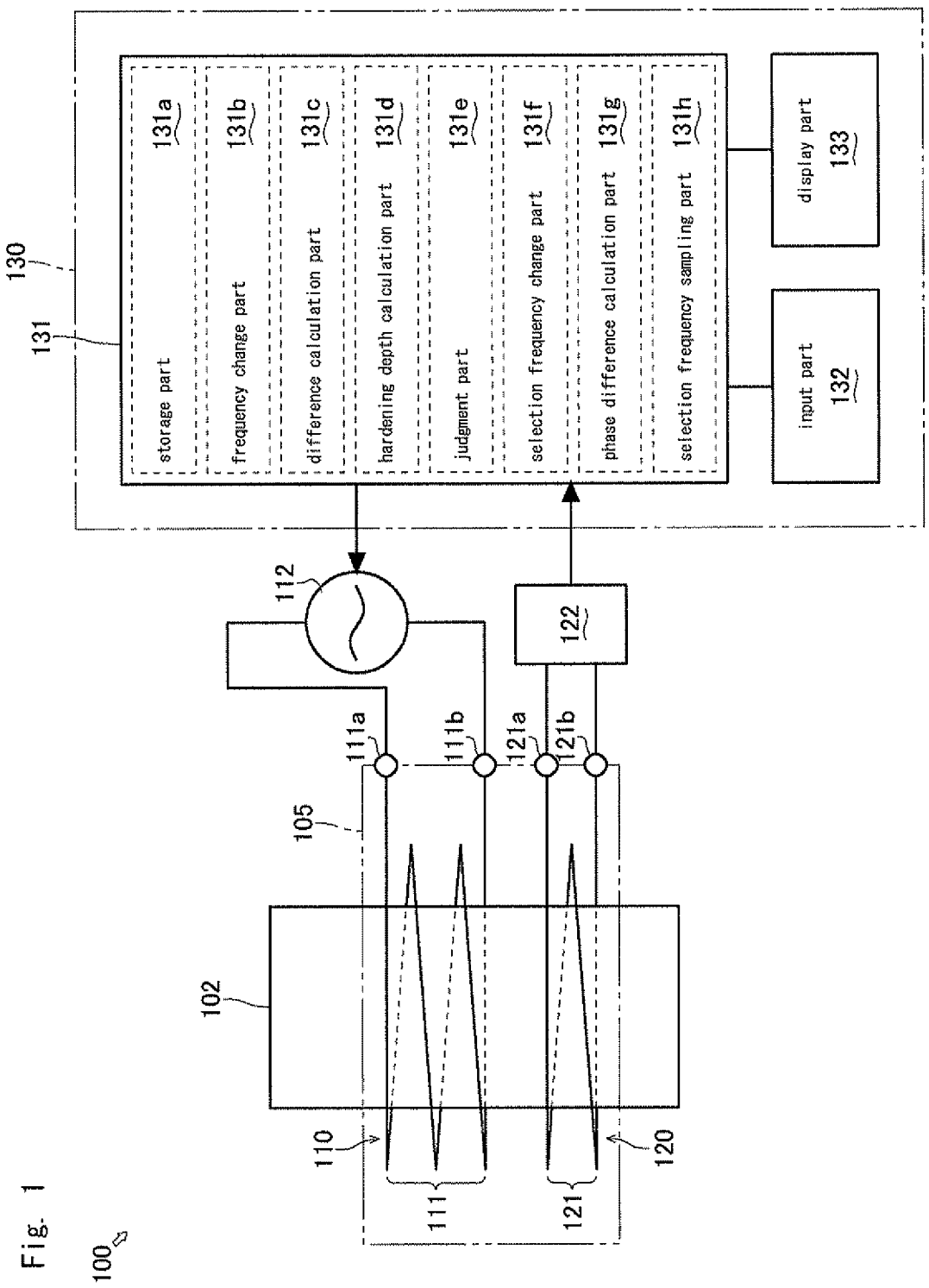
FIG. 1 is a drawing of a hardening depth measurement device to which an embodiment of a frequency selection method of eddy current measurement according to the present invention and an embodiment of a hardening depth measurement method according to the present invention are applied.

Explanation will be given below on construction of a hardening depth measurement device 100 to which an embodiment of a frequency selection method of eddy current measurement according to the present invention and an embodiment of a hardening depth measurement method according to the present invention are applied, referring FIG. 1.

The hardening depth measurement device 100 measures hardening depth a measurement object 102, and includes mainly magnetizer 110, a detector 120 and a controller 130.

Herein, the "hardening depth" corresponds to the "effective case depth" (the depth at which Vickers hardness is 450 Hv in steel with 0.45 wt % of carbon concentration) shown in the "methods of measuring case depth for steel hardened by flame or high frequency hardening process (JIS G 0559)" of Japanese Industrial Standards. However, the hardening depth according to the present invention is not limited thereto, and may alternatively correspond to the "total case depth (physical property (hardness) from a surface of case layer to a stock (base layer) or depth at the position at which difference of chemical property (macrostructure) cannot be distinguished)" shown in the "methods of measuring case depth for steel hardened by flame or high frequency hardening process (JIS G 0559)" of Japanese Industrial Standards, or may be determined with another method.

The measurement object 102 is formed by a metal material such as a steel material, and is hardened preferably.

The measurement object 102 in this embodiment is a drive shaft for a driving force transmission mechanism of a car, and is that S45C (about 0.45 wt % of carbon concentration), which is carbon steel for machine construction, is hardened with high frequency. However, the shape (type of members or the like) and material of the measurement object according to the present invention is not limited thereto, and includes widely members of metal materials which can be hardened (mainly, steel materials).

The measurement object of eddy current measurement to which the frequency selection method of eddy current measurement according to the present invention is applied is not limited to the "hardened member" as this embodiment, and includes things of various metal materials. As another embodiment of the measurement object according to the present invention, a thing whose surface is carburized, a thing whose surface is nitrided and the like are given.

The magnetizer 110 makes an alternating current magnetic field affect on the measurement object 102 so as to generate an induced current in the measurement object 102 (more strictly, in the surface and the inside of the measurement object 102).

The magnetizer 110 includes a magnetization coil 111, an alternator 112 and the like.

The magnetization coil 111 is an embodiment of a magnetization coil according to the present invention.

The magnetization coil 111 is formed by an electric conductor, and is applied thereon with alternating current magnetization signals of a plurality of different frequencies Fa, Fb, ... Fx so as to generate induced currents corresponding to the frequencies (eddy current) on the measurement object 102.

Herein, "apply alternating current magnetization signals" indicates to apply alternating current voltage of predetermined amplitude having predetermined frequency on the magnetization coil.

Terminals 111a and 111b are formed at both ends of the magnetization coil 111.

In this embodiment, as shown in FIG. 1, the measurement object 102 is inserted into the magnetization coil 111 and then the alternating current magnetization signals are applied on the magnetization coil 111. However, the hardening depth measurement device according to the present invention is not limited thereto, and, for example, may alternatively be constructed that the magnetization coil is arranged at predetermined distance from a plate surface of a plate-like measurement object and then the alternating current magnetization signals are applied on the magnetization coil.

The alternator 112 generates alternating current voltage of predetermined amplitude having predetermined frequency so as to apply the alternating current magnetization signal (alternating current voltage) on the magnetization coil 111. The alternator 112 is connected to the terminals 111a and 111b of the magnetization coil 111.

The alternator 112 can changes the frequency of the alternating current voltage within the range not less than 5 Hz and not more than 30 kHz, and can selectively the alternating current magnetization signals (alternating current voltage) of the plurality of different frequencies Fa, Fb, ... Fx within the range not less than 5 Hz and not more than 30 kHz on the magnetization coil 111.

In this embodiment, the range of the frequency of the alternating current magnetization signal applied on the magnetization coil of the hardening depth measurement device 100 is within the range not less than 5 Hz and not more than 30 kHz. However, the present invention is not limited thereto, and the range of the frequency of the alternating current magnetization signal can be selected suitably corresponding to the material, size, shape and the like of the measurement object.

The detector 120 detects induced voltage (detection signal) caused by the induced current generated in the measurement object 102 (more strictly, in the surface and the inside of the measurement object 102).

The detector 120 includes mainly a detection coil 121, a voltmeter 122 and the like.

The detection coil 121 is an embodiment of a detection coil according to the present invention.

The detection coil 121 is inserted thereto with the measurement object 102 and detects the detection signal caused by the induced current generated in the measurement object 102 (more strictly, in the surface and the inside of the measurement object 102).

Terminals 121a and 121b are formed at both ends of the detection coil 121.

The detection coil 121 and the magnetization coil 111 are arranged substantially concentrically.

In this embodiment, as shown in FIG. 1, the measurement object 102 is inserted into the detection coil 121 and then the detection signal is detected. However, the hardening depth measurement device according to the present invention is not limited thereto, and, for example, may alternatively be constructed that the detection coil is arranged at predetermined distance from a plate surface of a plate-like measurement object and then the detection signal is detected.

The voltmeter 122 is connected to the terminals 121a and 121b and exchanges the detection signal (induced voltage) detected by the detection coil 121 into a predetermined digital signal.

In this embodiment, the magnetization coil 111 as the magnetization coil and the detection coil 121 as the detection coil are housed in one housing 105, and the combination of the housing 105, the magnetization coil 111 and the detection coil 121 are referred to as the "eddy current sensor". However, the present invention is not limited thereto, and the magnetization coil and the detection coil may alternatively be housed respectively in separate housings.

The controller 130 controls action of the hardening depth measurement device 100 and calculates the hardening depth (obtains the measurement result of the hardening depth) of the measurement object 102 based on the detection signal detected by the detector 120.

The controller 130 includes mainly a control part 131, an input part 132, a display part 133 and the like.

The control part 131 can store various programs and the like therein, extract the programs, perform predetermined calculation according to the programs, and store the result of the calculation and the like.

Substantively, the control part 131 may be constructed that CPU, ROM, RAM, HDD and the like are connected to each other through a bus, or may alternatively be a one-chip LSI or the like.

The control part 131 in this embodiment is dedicated, but may alternatively be a commercial personal computer or work station in which the above programs and the like are stored.

The control part 131 is connected to the alternator 112 and can change the frequency and amplitude of the alternating current magnetization signal of the alternator 112 by transmitting a predetermined control signal to the alternator 112.

The control part 131 is connected to the voltmeter 122 so as to obtain "the detection signal (induced voltage) detected by the detection coil 121 and then exchanged into the predetermined digital signal by the voltmeter 122".

Functionally, the control part 131 includes a storage part 131a, a frequency change part 131b, a difference calculation part 131c, a hardening depth calculation part 131d, a judgment part 131e, a selection frequency change part 131f, a phase difference calculation part 131g and a selection frequency sampling part 131h.

Substantively, the control part 131 performed the predetermined calculation according to the programs and the like stored in the control part 131 so as to perform the functions as the storage part 131a, the frequency change part 131b, the difference calculation part 131c, the hardening depth calculation part 131d, the judgment part 131e, the selection frequency change part 131f, the phase difference calculation part 131g and the selection frequency sampling part 131h.

In the control part 131, the storage part 131a, the selection frequency change part 131f, the phase difference calculation part 131g and the selection frequency sampling part 131h collaborate so as to perform processes constituting the embodiment of the frequency selection method of the eddy current measurement according to the present invention.

In the control part 131, the storage part 131a, the frequency change part 131b, the difference calculation part 131c, the hardening depth calculation part 131d and the judgment part 131e collaborate so as to perform processes constituting the embodiment of the hardening depth calculation method of the eddy current measurement according to the present invention.

The concrete function of each of the storage part 131a, the frequency change part 131b, the difference calculation part 131c, the hardening depth calculation part 131d, the judgment part 131e, the selection frequency change part 131f, the phase difference calculation part 131g and the selection frequency sampling part 131h is described later.

The input part 132 is connected to the control part 131 so as to input various kinds of information, command and the like concerning the measurement of hardening depth with the hardening depth measurement device 100 into the control part 131.

The input part 132 in this embodiment is dedicated, but similar effect can be obtained by, for example, commercial keyboard, mouse, pointing device, button, switch or the like.

The display part 133 displays, for example, the input contents from the input part 132 to the control part 131, the action situation of the hardening depth measurement device 100, the measurement result of the hardening depth of the measurement object 102 and the like.

The display part 133 in this embodiment is dedicated, but similar effect can be obtained by, for example, commercial liquid crystal display (LCD), CRT display (cathode ray tube display) or the like.

In this embodiment, the input part 132 and the display part 133 are separated. However, the present invention is not limited thereto, and it may alternatively be constructed that the function of information input and the function of information display is combined (the input part and the display part are constructed integrally).

Explanation will be given below on measurement principle of the hardening depth measurement device 100 referring FIGS. 2 to 4.

Figure 2:
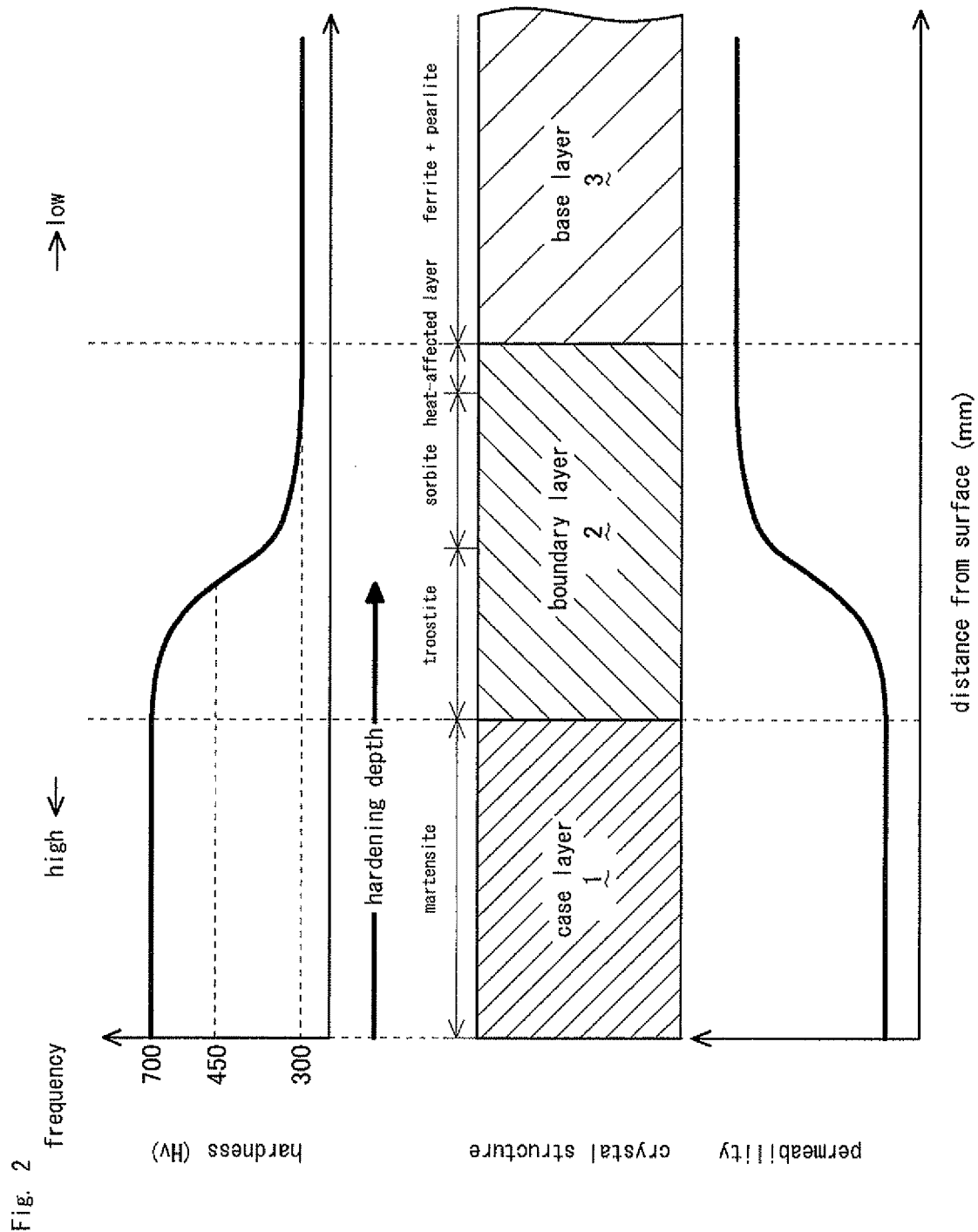
FIG. 2 is a diagram of relation between crystal structure, hardness and permeability of a measurement object and distance from the surface thereof.

FIG. 2 is a schematic diagram of relation between crystal structure (layer), hardness and permeability of the measurement object 102 and distance (depth) from the surface of the measurement object 102.

As shown in FIG. 2, the crystal structure of the measurement object 102 includes three layers, a case layer 1, a boundary layer 2 and a base layer 3 in this order from the side of the surface.

The case layer 1 is formed in the vicinity of the surface of the measurement object 102, and the cooling speed at the time of the hardening process is the largest at the case layer 1.

The main crystal structure of the case layer 1 is martensite.

The boundary layer 2 is formed at a portion farther from the surface than the case layer 1 and at which the cooling speed at the time of the hardening process is smaller than the case layer 1.

In this embodiment, S45C which is the material forming the measurement object 102 is classified into medium carbon steel (about 0.45 wt % of carbon concentration), and the main crystal structure of the boundary layer 2 is fine pearlite formed from troostite and sorbite, a heat-affected layer and the like.

The crystal structure of the boundary layer is different corresponding to composition of material of the measurement object, and is not limited to this embodiment.

As another example of the crystal structure of the boundary layer, upper bainite, lower bainite and the like are given.

The base layer 3 is formed at a portion farther from the surface than the boundary layer 2 and at which the cooling speed at the time of the hardening process is smaller than the boundary layer 2.

In this embodiment, S45C which is the material forming the measurement object 102 is classified into medium carbon steel, and the main crystal structure of the base layer 3 is mixed structure of pearlite and ferrite.

The crystal structure of the base layer is different corresponding to composition of material of the measurement object, and is not limited to this embodiment.

As another example of the crystal structure of the base layer, pearlite structure, mixed structure of ferrite and cementite, and the like are given.

As shown in FIG. 2, the hardness (Vickers hardness) of the measurement object 102 is closely related with the crystal structure.

The martensite which constitutes the case layer 1 generally has small crystal particle size and large dislocation density, whereby the hardness thereof is high. However, generally, the hardness of the case layer 1 slightly changes when the distance from the surface changes. The hardness of the case layer 1 in this embodiment is about 600 to 700 (Hv) in Vickers hardness.

Compared with the martensite which constitutes the case layer 1, the fine pearlite and heat-affected layer which constitute the boundary layer 2 generally have relatively large crystal particle size and small dislocation density, whereby the hardness thereof is also relatively low.

The larger (deeper) the distance from the surface is, the smaller the hardness of the boundary layer 2 is.

Compared with the fine pearlite and heat-affected layer which constitute the boundary layer 2, the mixed structure of pearlite and ferrite which constitute the base layer 3 generally has relatively large crystal particle size, whereby the hardness thereof is also relatively low. However, generally, the hardness of the base layer 3 slightly changes when the distance from the surface changes. The hardness of the base layer 3 in this embodiment is about 300 (Hv) in Vickers hardness.

As shown in FIG. 2, the permeability of the measurement object 102 is closely related with the crystal structure. That is because the permeability of the measurement object 102 generally tends to be small when the crystal particle size of the measurement object 102 is small, and hardness of a steel material generally tends to be small when crystal particle size thereof is small. Then, the permeability and hardness of the measurement object 102 are substantially inversely proportional to each other.

Generally, the permeability of the case layer 1 is low and slightly changes when the distance from the surface changes.

The permeability of the boundary layer 2 is large relatively to that of the case layer 1, and the larger (deeper) the distance from the surface is, the larger the permeability of the boundary layer 2 is.

The permeability of the base layer 3 is large relatively to those of the case layer 1 and the boundary layer 2, and generally slightly changes when the distance from the surface changes.

Figure 3:
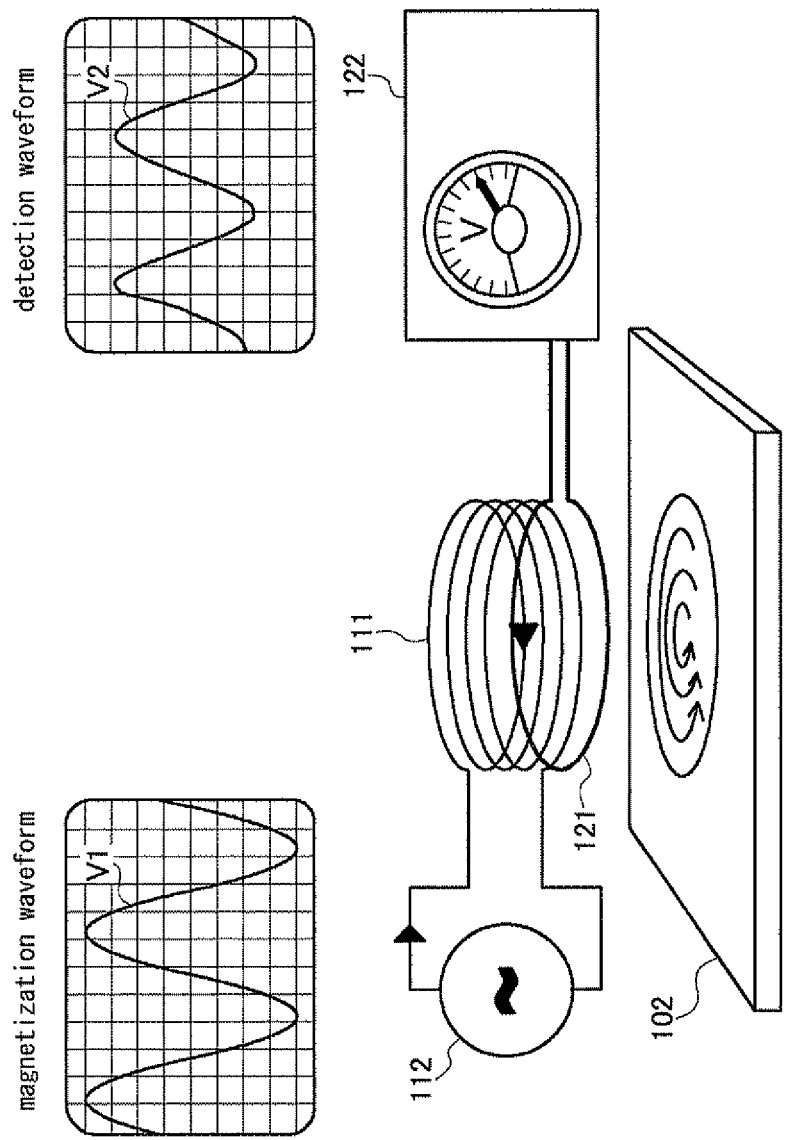
FIG. 3 is a drawing of measurement principle of the hardening depth measurement device.

As shown in FIG. 3, in the state that the measurement object 102 is arranged in the vicinity of the magnetization coil 111 and the detection coil 121, when the alternating current magnetization signals of the plurality of frequencies Fa, Fb, . . . Fx are applied on the magnetization coil 111, a magnetic field is generated around the magnetization coil 111 and an induced current (eddy current) is generated in the surface and inside of the measurement object 102 (especially, in the part surrounded by the magnetization coil 111).

Then, magnetic flux generated by the induced current penetrates the detection coil 121 so as to generate the detection signal (induced voltage) in the detection coil 121.

By the skin effect, there is a tendency that, as the frequency of the alternating current magnetization signal applied on the magnetization coil 111 is increased, the induced current (eddy current) concentrates to the surface of the measurement object 102 and depth of penetration δ of the induced current (eddy current) is decreased ($\delta=(\pi*Fn*\mu*\sigma)-0.5$; $\mu$ is permeability and $\sigma$ is conductivity).

Accordingly, by changing the frequency of the alternating current magnetization signal, the depth of penetration 6 of the induced current (eddy current) can be changed. The depth of penetration 6 of the induced current (eddy current) corresponds to the depth from the surface of the measurement object.

Phase difference X between the alternating current magnetization signal and the detection signal tends to be proportional to depth D from the surface and inversely proportional to the depth of penetration δ.

Figure 4:
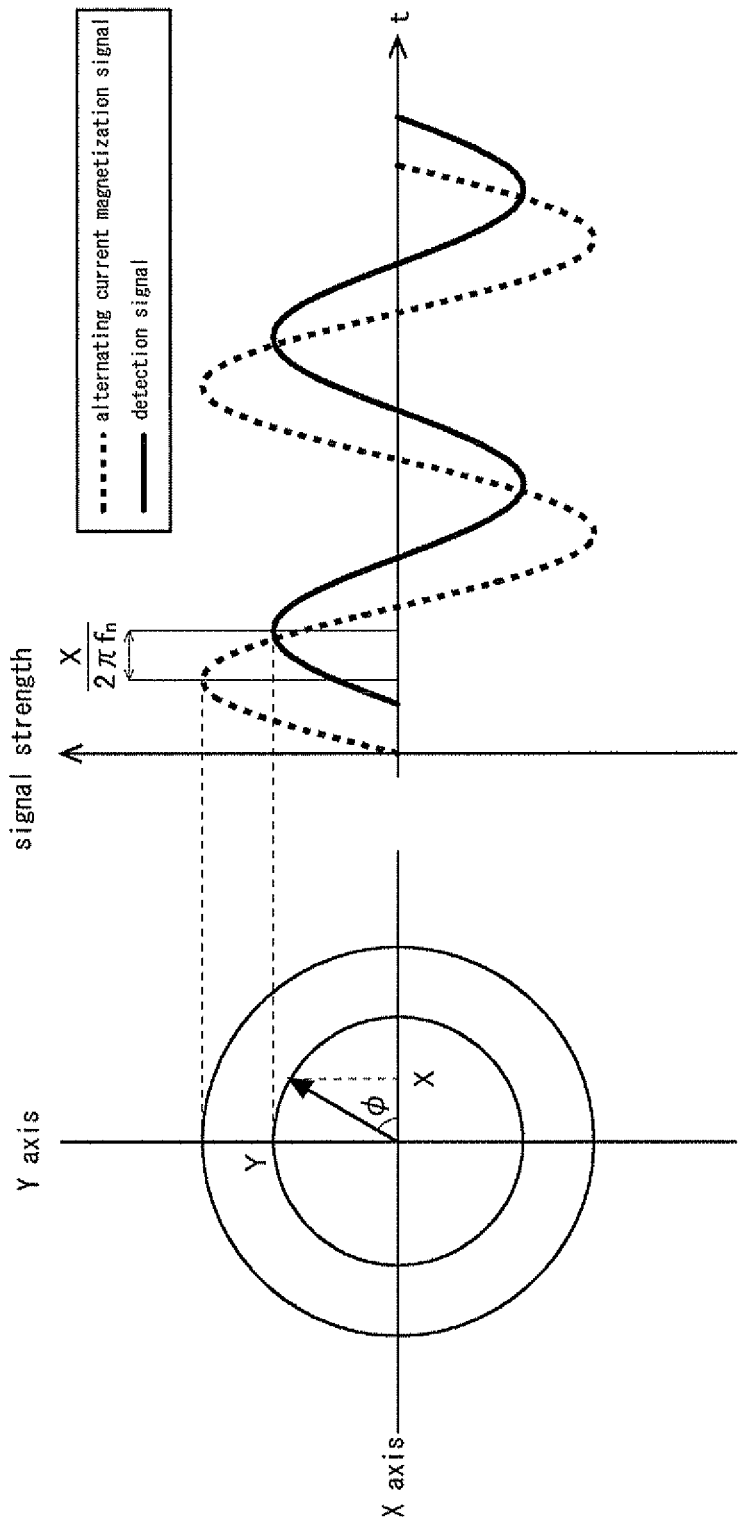
FIG. 4 is a diagram of relation between an alternating current magnetization signal and detection signal.

As shown in FIG. 4, the detection signal has predetermined amplitude Y and the predetermined phase difference X to the alternating current magnetization signal.

The permeability of the measurement object 102 is in correlation with (1) the amplitude Y and (2) the phase difference X of the detection signal to the alternating current magnetization signal.

Then, the operation that the detection signal corresponding to the frequency of the alternating current magnetization signal is detected while the frequency is changed suitably so as to obtain the amplitude Y and the phase difference X of the detection signal corresponds to the operation to obtain the permeability of the portion in the measurement object 102 at which the depth from the surface corresponds to the depth of penetration at each frequency of the alternating current magnetization signal.

Accordingly, by obtaining the relation between the frequency (that is, depth of penetration) of the alternating current magnetization signal of the measurement object 102 and the amplitude Y and the phase difference X of the detection signal corresponding to the frequency, the hardening depth of the measurement object 102 can be obtained noncontactly (nondestructively).

Explanation will be given below on an embodiment of the frequency selection method of the eddy current measurement according to the present invention, referring FIGS. 1, 5 and 6.

The embodiment of the frequency selection method of the eddy current measurement according to the present invention is the method for selecting combination of two frequencies (first frequency and second frequency) used for measuring the hardening depth of the measurement object 102 with the hardening depth measurement device 100, and the selection is performed before the measurement of the hardening depth of the measurement object 102 with the hardening depth measurement device 100.

Figure 5:
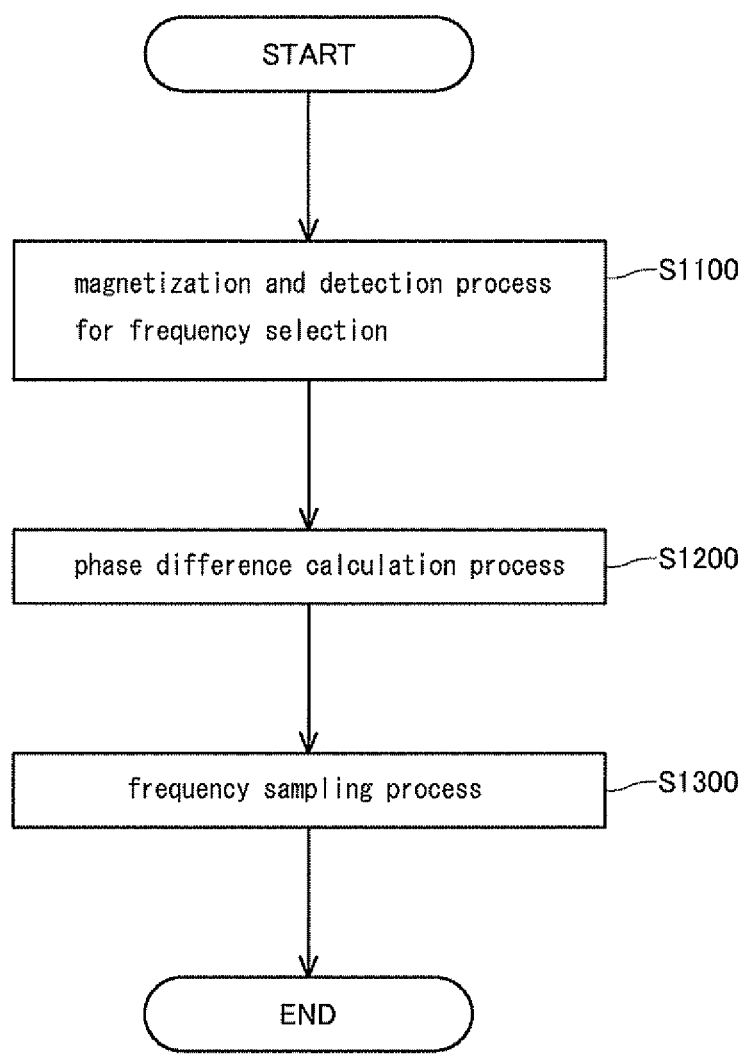
FIG. 5 is a flow chart of an embodiment of the frequency selection method of eddy current measurement.

As shown in FIG. 5, the embodiment of the frequency selection method of the eddy current measurement according to the present invention includes a magnetization and detection process for frequency selection S1100, a phase difference calculation process S1200 and a frequency sampling process S1300.

In the magnetization and detection process for frequency selection S1100, the magnetization coil 111 applies the alternating current magnetization signals of three or more different frequencies on the measurement object 102 so as to generate the induced currents corresponding respectively to the three or more different frequencies on the measurement object 102, and the detection coil 121 detects the detection signals caused by the induced currents corresponding respectively to the three or more different frequencies.

In the magnetization and detection process for frequency selection S1100, the selection frequency change part 131f of the control part 131 transmits a control signal that 24 kinds of frequencies Fa, Fb, ... Fx (see FIG. 6) are applied in turn to the alternator 112.

The alternator 112 receiving the control signal from the selection frequency change part 131f of the control part 131 applies alternating voltage of the 24 kinds of frequencies Fa, Fb, ... Fx on the magnetization coil 111 following the control signal, and the magnetization coil 111 applies the alternating current magnetization signals of the 24 kinds of frequencies Fa, Fb, ... Fx on the measurement object 102 in turn.

As a result, the induced currents (eddy currents) corresponding to the frequencies are generated on the measurement object 102 in turn. At this time, the detection coil 121 detects the detection signals corresponding to the frequencies.

The detection signals detected by the detection coil 121 are exchanged into the predetermined digital signals (digital signals of a form which can be received by the control part 131) by the voltmeter 122 and then transmitted to the control part 131.

The detection signals transmitted to the control part 131 are stored in the storage part 131a of the control part 131.

In this case, each of the detection signals stored in the storage part 131a has "corresponding frequency", "amplitude" and "phase" as parameters.

The storage part 131a stores various parameters (numerical values), records of action situation, operation results (calculation results) and the like used in the control and operation with the control part 131.

Substantively, the storage part 131a includes a storage media such as HDD (hard disk drive), CD-ROM, DVD-ROM or the like.

When the magnetization and detection process for frequency selection S1100 is finished, the process flow shifts to the phase difference calculation process S1200.

In the phase difference calculation process S1200, based on "the detection signals caused by the three or more different frequencies" detected in the magnetization and detection process for frequency selection S1100, phase differences between the alternating current magnetization signals and the phase difference of the detection signals respectively corresponding to the three or more different frequencies are calculated.

In the phase difference calculation process S1200, based on "the action records of the alternator 112" and "the detection signals detected by the detection coil 121" stored in the storage part 131a, the phase difference calculation part 131g calculates the phase differences Xa, Xb, ... Xn between the alternating current magnetization signals and the detection signals (the gaps of the phase of the detection signals about the phase of the alternating current magnetization signals) respectively corresponding to the 24 kinds of frequencies Fa, Fb, ... Fx.

The calculated phase differences Xa, Xb, ... Xn are stored in the storage part 131a of the control part 131. At this time, each of the phase differences Xa, Xb, ... Xn is stored while associated with the corresponding frequency.

When the phase difference calculation process S1200 is finished, the process flow shifts to the frequency sampling process S1300.

Figure 6:
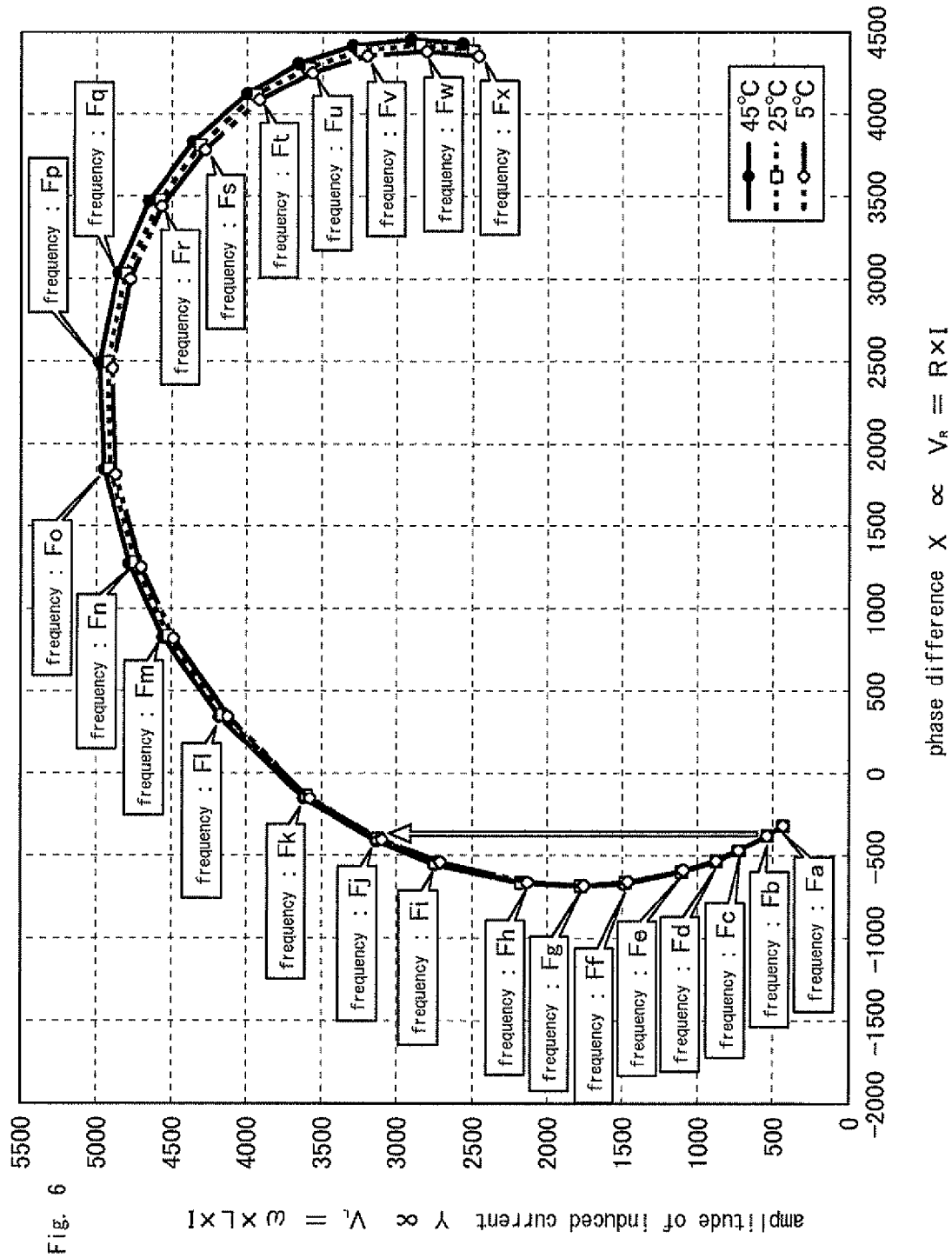
FIG. 6 is a diagram of relation between phase difference X and amplitude Y.

As shown in FIG. 6, in this embodiment, the detection signals corresponding to the frequencies are plotted on the phase difference-amplitude plane (a plane that the phase difference X between the alternating current magnetization signal and the detection signal is taken along the axis of abscissas and the amplitude Y is taken along the axis of ordinates), and the plotted points are connected with a polygonal line in the order of magnitude of frequency from the lowest (in the order of Fa, Fb, ... Fx). Then, the polygonal line shows below tendency.

In the area that the frequency is relative low (Fa to Fk), the polygonal line is slightly projected toward the minus side of the phase difference. Namely, the change amount of the phase difference following the increase of the frequency is relative small, and the increase amount of the amplitude of the induced current (the amplitude of the detection signal) is relative large. The phase difference is minus.

In the area that the frequency is middle (Fl to Ft), the polygonal line is projected toward the plus side of the phase difference. Namely, the increase amount of the amplitude of the induced current is relative small, and the change amount of the phase difference following the increase of the frequency is relative large.

In the area that the frequency is relative high (Fu to Fx), the polygonal line is slightly projected toward the plus side of the phase difference. Namely, the change amount of the phase difference following the increase of the frequency is relative small, and the decrease amount of the amplitude of the induced current (the amplitude of the detection signal) is relative large.

As shown in FIG. 6, in this embodiment, the results of the magnetization and detection process for frequency selection S1100 and the phase difference calculation process S1200 are plotted respectively in the three eases that the environment temperature is 5° C. (supposing the ambient temperature in the factory at winter), 25° C. (supposing the ambient temperature in the factory at spring or autumn), and 45° C. (supposing the ambient temperature in the factory at summer). The temperature of the measurement object 102 is set the same as the environment temperature.

As shown in FIG. 6, in the area that the frequency is relative low (Fa to Fk), the positions of the points corresponding to the same frequency are almost the same even if the temperature is changed (the temperature dependency of the phase difference and the amplitude is small).

On the other hand, in the area that the frequency is middle (Fl to Ft), the positions of the points corresponding to the same frequency tend to be slightly dispersed according to the change of the temperature.

In the area that the frequency is relative high (Fu to Fx), the positions of the points corresponding to the same frequency are widely dispersed according to the temperature (the temperature dependency of the phase difference and the amplitude is large).

The causes of the tendency shown in FIG. 6 are given below. Generally, the area that the frequency is relative low (Fa to Fk) corresponds to the portion that the distance from the surface of the measurement object 102 is relatively large (deep) so that the permeability is dominant. On the other hand, the area that the frequency is high (Fu to Fx) corresponds to the portion that the distance from the surface of the measurement object 102 is relatively small (shallow) so that the conductivity is dominant. The conductivity is indicated by an inverse of electric resistivity and the electric resistivity is generally a function of the temperature (has the temperature dependency).

The phase difference X as the axis of abscissas in the phase difference-amplitude plane shown in FIG. 6 is indicated with a relational expression shown in below formula 3, and the amplitude Y as the axis of ordinates is indicated with a relational expression shown in below formula 4.

$$X \approx V_R = R \times I \quad \text{[Formula 3]}$$

$$Y \approx V_L = \omega \times L \times I = 2\pi F \times L \times I \quad \text{[Formula 4]}$$

Herein, R in the formula 3 indicates the resistance component of the detection coil 121, $V_R$ in the formula 3 indicates the terminal electromotive force of the detection coil 121, L in the formula 4 indicates the inductance component of the detection coil 121, I in the formulas 3 and 4 indicates the current value flowing in the detection coil 121.

Accordingly, the phase difference-amplitude plane shown in FIG. 6 is substantially analogous to an impedance plane of the detection coil 121.

The temperature dependency of the measurement result which is a problem of the eddy current measurement is caused by the temperature dependency of the resistance component in the impedance of the detection coil 121 and the measurement object 102.

Then, by selecting the combination of frequencies which can cancel the resistance component in the impedance of the detection coil 121 and the measurement object 102, the problem of the temperature dependency of the measurement result of the eddy current measurement can be solved.

In the frequency sampling process S1300, within the phase differences between the alternating current magnetization signals and the detection signals (in this embodiment, Xa, Xb, . . . Xn) respectively corresponding to "the three or more different frequencies (in this embodiment, Fa, Fb, Fx)" calculated in the phase difference calculation process S1200, combinations of two frequencies each of which makes the difference of the phase differences within the predetermined range are extracted, and in each of the combinations, lower one of the two frequencies is referred to as "first frequency" and higher one thereof is referred to as "second frequency", whereby those are to be used for the measurement of the hardening depth of the measurement object 102 with the hardening depth measurement device 100.

In the frequency sampling process S1300, the selection frequency sampling part 131*h* of the control part 131 calculates the all differences of the phase differences Xa, Xb, . . . Xn stored in the storage part 131*a* (concretely, calculates Xa-Xb, Xa-Xc, . . . Xv-Xx, Xw-Xx). In this embodiment, two of 24 kinds of the phase differences are selected and the difference thereof is calculated so that the calculated differences of the phase differences are 276 kinds (−24*23/2).

Next, the selection frequency sampling part 131*h* extracts the combinations of two frequencies each of which makes the difference of the phase differences within the "predetermined range" (the difference is not less than the lowest value of the predetermined range and not more than the highest value thereof).

Herein, the "predetermined range" preferably includes zero and each of the lowest value and the highest value as close to zero as possible. That is because the closer to zero the difference of the phase differences (the smaller the absolute value of the difference of the phase differences is) is, the closer to zero the component along the axis of abscissas of the vector (white arrow) connecting the plots respectively corresponding to the two phase differences on the phase difference-amplitude plane shown in FIG. 6 (the component analogous to the resistance component in the impedance) is, whereby the resistance component in the impedance of the detection coil 121 and the measurement object 102 is canceled.

In this embodiment, "the combination of frequencies Fb and Fj", "the combination of frequencies Fd and Fi" and "the combination of frequencies Ff and Fh" that the values of the phase difference X are close to each other are extracted as "the combination which make the difference of the phase differences within the predetermined range" (see FIG. 6).

Subsequently, the selection frequency sampling part 131*h* except the combination including the frequency out of the supposed range of the hardening depth of the measurement object 102 from the extracted three "combinations which make the difference of the phase differences within the predetermined range", extracts the combination having the largest difference of the frequencies, and refers to the lower one of the two frequencies of the extracted combination as "the first frequency" and refers to the higher one thereof as "the second frequency".

Herein, "the supposed range of the hardening depth of the measurement object 102" is the range of the hardening depth which is supposable in the case that the measurement object 102 is hardened according to the normal work processes.

In this embodiment, each of "the combination of frequencies Fb and Fj", "the combination of frequencies Fd and Fj" and "the combination of frequencies Ff and Fh" does not include the frequency out of the supposed range of the hardening depth of the measurement object 102 so that the selection frequency sampling part 131h extracts "the combination of frequencies Fb and Fj" having the largest difference of the frequencies and selects the frequency Fb as the first frequency and the frequency Fj as the second frequency.

The selection result of the first frequency and the second frequency is stored in the storage part 131a.

By extracting the combination having the largest difference of the frequencies, the range of the depth of penetration of induced current generated in the measurement object 102 in the case of the measurement of the hardening depth of the measurement object 102 with the hardening depth measurement device 100 is as wide as possible, whereby the measurement result is made to reflect the wide range of the measurement object 102 in the depth direction.

As mentioned above, in the embodiment of the frequency selection method of the eddy current measurement according to the present invention, the magnetization coil 111 applies the alternating current magnetization signals of the first frequency and the second frequency different from the first frequency on the measurement object 102 so as to generate the induced currents including the eddy currents respectively corresponding to the first frequency and the second frequency in the measurement object 102; the detection coil 121 detects the detection signals caused by the induced currents respectively corresponding to the first frequency and the second frequency; the phase difference D shown in the formula 1 is calculated based on the amplitude Y1 of the detection signal corresponding to the first frequency, the phase difference X1 of the alternating current magnetization signal and the detection signal corresponding to the first frequency, the amplitude Y2 of the detection signal corresponding to the second frequency, and the phase difference X2 between the alternating current magnetization signal and the detection signal corresponding to the second frequency; and the measurement object 102 (the hardening depth thereof) is measured based on the phase difference D. The embodiment of the method includes the magnetization and detection process for frequency selection S1100 that the magnetization coil 111 applies the alternating current magnetization signals of the three or more different frequencies (in this embodiment, Fa, Fb, . . . Fx) on the measurement object 102 so as to generate the induced currents respectively corresponding to the three or more different frequencies in the measurement object 102 and the detection coil 121 detects the detection signals caused by the induced currents respectively corresponding to the three or more different frequencies; the phase difference calculation process S1200 that the phase differences between the alternating current magnetization signals and the detection signals respectively corresponding to the three or more different frequencies are calculated based on "the detection signals caused by the induced currents respectively corresponding to the three or more different frequencies" detected in the magnetization and detection process for frequency selection S1100; and the frequency sampling process S1300 that the combination of two frequencies which make the difference of the phase differences within the predetermined range is extracted from the phase differences (in this embodiment, Xa, Xb, . . . Xn) between the alternating current magnetization signals and the detection signals respectively corresponding to "the three or more different frequencies (in this embodiment, Fa, Fb, . . . Fx)" calculated in the phase difference calculation process S1200 and the lower one of the two frequencies of the combination is referred to as "the first frequency" and the higher one thereof is referred to as "the second frequency" used for the measurement of hardening depth of the measurement object 102 with the hardening depth measurement device 100.

The construction brings below merit.

By only calculating the phase differences between the alternating current magnetization signals and the detection signals respectively corresponding to the three or more different frequencies and extracting the combination of two frequencies which make the difference within the predetermined range, the combination of two suitable frequencies can be selected appropriately and easily while the temperature dependency of the measurement accuracy is reduced or eliminated, whereby laborsaving of the selection work of the combination of two suitable frequencies can be obtained (the man-power and time for the selection work can be reduced).

Explanation will be given below on an embodiment of the hardening depth measurement method according to the present invention, referring FIGS. 1, 7, 8 and 9.

The embodiment of the hardening depth measurement method according to the present invention is a method for measuring the hardening depth of the measurement object 102 with the hardening depth measurement device 100 (see FIG. 1).

Figure 7:
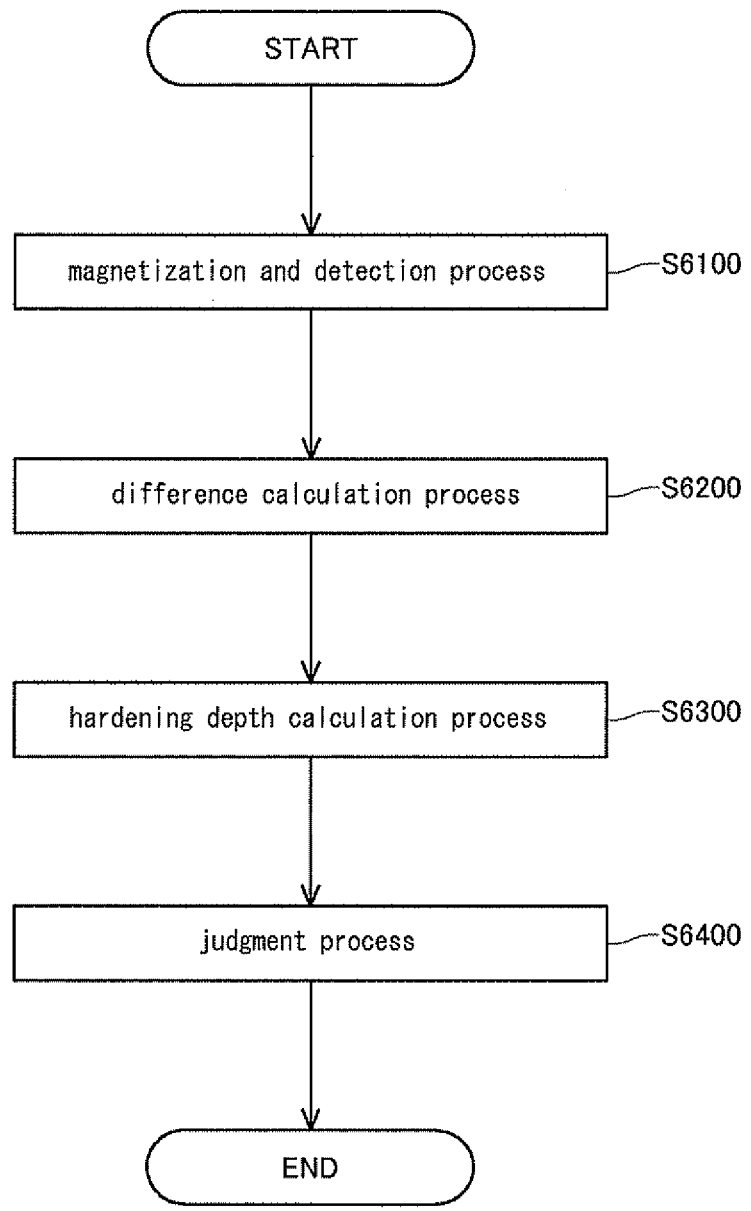
FIG. 7 is a flow chart of an embodiment of the hardening depth measurement method.

As shown in FIG. 7, the embodiment of the hardening depth measurement method according to the present invention includes a magnetization and detection process S6100, a difference calculation process S6200, a hardening depth calculation process S6300 and a judgment process S6400.

In the magnetization and detection process S6100, the magnetization coil 111 applies the alternating current magnetization signals of the first frequency (in this embodiment, frequency Fb) and the second frequency (in this embodiment, frequency Fj) different from the first frequency on the measurement object 102 so as to generate the induced currents including the eddy currents respectively corresponding to the first frequency and the second frequency in the measurement object 102, whereby the detection signals caused by the induced currents respectively corresponding to the first frequency and the second frequency by the detection coil 121.

In the magnetization and detection process S6100, the frequency change part 131b transmits a control signal that the alternator 112 generates the alternating voltage corresponding to the first frequency based on "the selection result of the first frequency and the second frequency" stored in the storage part 131a.

According to the control signal from the frequency change part 131b, the alternator 112 applies the first frequency (frequency Fb) and the second frequency (frequency Fj) in turn on the magnetization coil 111, and the magnetization coil 111 applies the alternating current magnetization signals of the first frequency (frequency Fb) and the second frequency (frequency Fj) in turn on the measurement object 102.

As a result, the induced currents (eddy currents) corresponding to the first frequency (frequency Fb) and the second frequency (frequency Fj) are generated in turn on the measurement object 102. At this time, the detection coil 121 detects the detection signals corresponding to the first frequency (frequency Fb) and the second frequency (frequency Fj) in turn.

The detection signals corresponding to the first frequency (frequency Fb) and the second frequency (frequency Fj) detected by the detection coil 121 are exchanged into the predetermined digital signals (digital signals of a form which can be received by the control part 131) by the voltmeter 122 and then transmitted to the control part 131.

The detection signals corresponding to the first frequency (frequency Fb) and the second frequency (frequency Fj) and transmitted to the control part 131 are stored in the storage part 131a of the control part 131.

When the magnetization and detection process S6100 is finished, the process flow shifts to the difference calculation process S6200.

In the difference calculation process S6200, the difference D shown in the formula 1 is calculated based on the amplitude Y1 of the induced current corresponding to the first frequency (frequency Fb), the phase difference X1 of the alternating current magnetization signal and the detection signal corresponding to the first frequency, the amplitude Y2 of the induced current corresponding to the second frequency (frequency Fj), and the phase difference X2 between the alternating current magnetization signal and the detection signal corresponding to the second frequency.

$$D = \frac{\sqrt{X_1^2 + Y_1^2} - \sqrt{X_2^2 + Y_2^2}}{\sqrt{X_2^2 + Y_2^2}}$$ [Formula 1]

In the difference calculation process S6200, the difference calculation part 131c calculates the amplitude Y1 of the detection signal corresponding to the first frequency (frequency Fb), the phase difference X1 of the alternating current magnetization signal and the detection signal corresponding to the first frequency, the amplitude Y2 of the detection signal corresponding to the second frequency (frequency Fj), and the phase difference X2 between the alternating current magnetization signal and the detection signal corresponding to the second frequency based on the detection signals corresponding to the first frequency (frequency Fb) and the second frequency (frequency Fj) stored in the storage part 131a. Calculated Y1, X1, Y2 and X1 are stored in the storage part 131a suitably.

Next, the difference calculation part 131c substitutes calculated Y1, X1, Y2 and X1 for the relational expression of the difference D and Y1, X1, Y2 and X1 shown in the formula 1 so as to calculate the difference D. The calculated difference D is stored in the storage part 131a suitably.

When the difference calculation process S6200 is finished, the process flow shifts to the hardening depth calculation process S6300.

While the amplitude of the detection signal is taken along a Y axis and the phase difference between the alternating current magnetization signal and the detection signal is taken along a X axis, the difference D shown in the formula 1 is the result of calculation that the length of the vector (X2, Y2) according to the second frequency $((X2^2+Y2^2)^{0.5})$ is subtracted from the length of the vector (X1, Y1) according to the first frequency $((X1^2+Y1^2)^{0.5})$, and the subtraction result is divided by the length of the vector according to the second frequency.

The crystal structure from the surface to the depth of penetration corresponding to the first frequency of the measurement object 102 and the influence of temperature of the crystal structure are reflected in the vector according to the first frequency.

The crystal structure from the surface to the depth of penetration corresponding to the second frequency of the measurement object 102 and the influence of temperature of the crystal structure are reflected in the vector according to the second frequency.

Since the first frequency is lower than the second frequency, the depth of penetration generated in the measurement object 102 by the alternating current magnetization signal of the first frequency is larger (deeper) than the depth of penetration generated in the measurement object 102 by the alternating current magnetization signal of the second frequency.

Then, by subtracting the length of the vector according to the second frequency from the length of the vector according to the first frequency, the information about the portion shallow from the surface of the measurement object 102, which is included in the vector according to the first frequency and the vector according to the second frequency commonly, can be canceled so as to emphasize the information about the portion in the vicinity of the hardening depth which is closely related with the measurement of the hardening depth.

Especially, since the temperature of the measurement object 102 is changed by the heat conduction between the surface of the measurement object 102 and the ambient atmosphere, the temperature change of the portion shallow from the surface of the measurement object 102 (the vicinity of the surface) tends to be larger than that of the portion deep from the surface (bulk), whereby the temperature change of the portion shallow from the surface of the measurement object 102 (the vicinity of the surface) contributes more to the reduction of the measurement accuracy.

Then, by canceling the information about the portion shallow from the surface of the measurement object 102, which is included in the vector according to the first frequency and the vector according to the second frequency commonly, large effect can be obtained on the suppression of reduction of the measurement accuracy of the hardening depth caused by the temperature change of the measurement object 102.

The length of the vector according to the second frequency is subtracted from the length of the vector according to the first frequency and the subtraction result is divided by the length of the vector according to the second frequency, whereby the effect of temperature change on the emphasized "information about the vicinity of the hardening depth" is suppressed further.

In the hardening depth calculation process S6300, the difference D calculated in the difference calculation process S6200 is substituted for the relational expression of the difference D, the hardening depth H of the measurement object 102, and constants A and B shown in formula 2 so as to calculate the hardening depth H of the measurement object 102.

$$D = A \times H^3 + B$$ [Formula 2]

The constants A and B in the formula 2 are previously determined by performing experimentation with a standard measurement object.

Herein, the "standard measurement object" is a member of the same material and shape as the measurement object and applied thereon the same heat treatment as the measurement object.

In the hardening depth calculation process S6300, the hardening depth calculation part 131d substitutes the difference D calculated by the difference calculation part 131c for "the relational expression of the hardening depth H and the difference D (in more detail, the constants A and B)" shown in formula 2 so as to calculate the hardening depth H. The calculated hardening depth H is stored in the storage part 131a suitably.

When the hardening depth calculation process S6300 is finished, the process flow shifts to the judgment process S6400.

Figure 8:
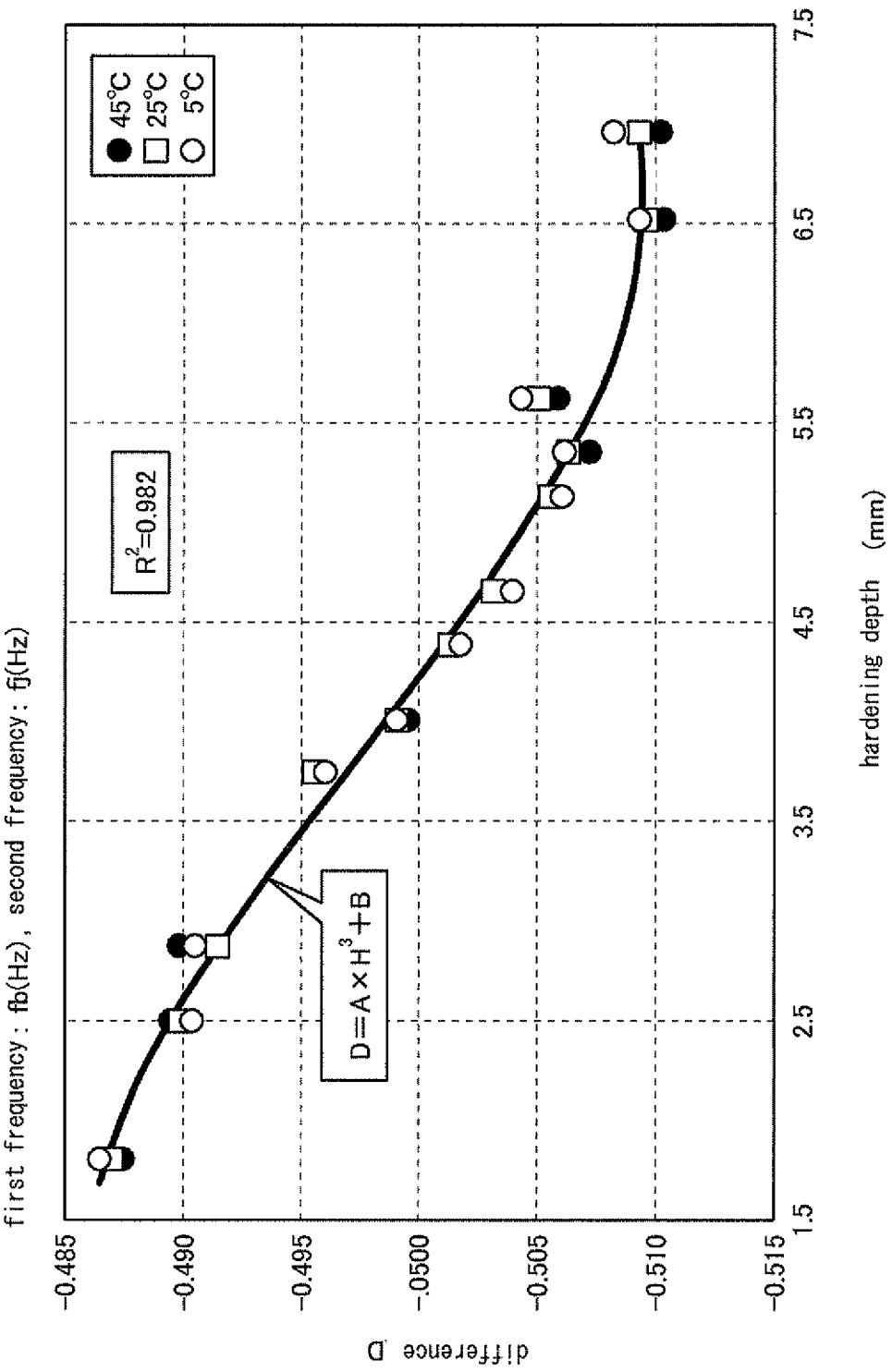
FIG. 8 is a diagram of relation between hardening depth H and difference D.

FIG. 8 is a graph of relation between the hardening depth H and the difference D of the measurement object 102 at every measurement portion in the case that the environment temperature is 5° C., 25° C. and 45° C. The hardening depth H on the axis of abscissas in FIG. 8 indicates the hardening depth at every measurement portion obtained by cutting the measurement portion of the measurement object 102 and measuring the Vickers hardness of the cut surface.

As shown in FIG. 8, among data of the same measurement portion (data at the same value of the axis of abscissas), the difference D changes slightly when the temperature changes, whereby the temperature dependency of the difference D is found to be small.

As shown in FIG. 8, in the case that the relation between the hardening depth H and the difference D is approximated to the cubic function shown in the formula 2, higher correlation ($R^2=0.982$) of the hardening depth at every measurement portion obtained by cutting the measurement portion of the measurement object 102 and measuring the Vickers hardness of the cut surface is obtained compared with the case that the relation between the hardening depth H and the difference D is approximated to a linear function (straight line).

Accordingly, by calculating the hardening depth H by substituting the difference D for the cubic function shown in the formula 2, the hardening depth H of the measurement object 102 can be measured with high accuracy noncontactly (nondestructively).

The approximation of the relation between the hardening depth H and the difference D to the cubic function shown in the formula 2 is suitable for the measurement principle of the measurement method such as the present invention that the hardening depth H is measured with the two frequencies, the first frequency and the second frequency.

Namely, since the first frequency and the second frequency respectively correspond to the two different depths of penetration of the induced current to the measurement object 102, in the case of the approximation to the cubic function, two inflection points of the cubic function are arranged in the vicinity of the depths of penetration respectively corresponding to the first frequency and the second frequency so that the part between the two inflection points can be approximated substantially to a straight line.

The part of the cubic function except for the part between the two inflection points has the tendency that the hardening depth changes widely by slight change of the difference. Then, by setting the part between the two inflection points of the cubic function as the tolerance of the hardening depth and setting the part of the cubic function except for the part between the two inflection points as the outside of the tolerance of the hardening depth, the measurement object that the hardening depth is out of the tolerance can be detected more certainly.

Figure 9:
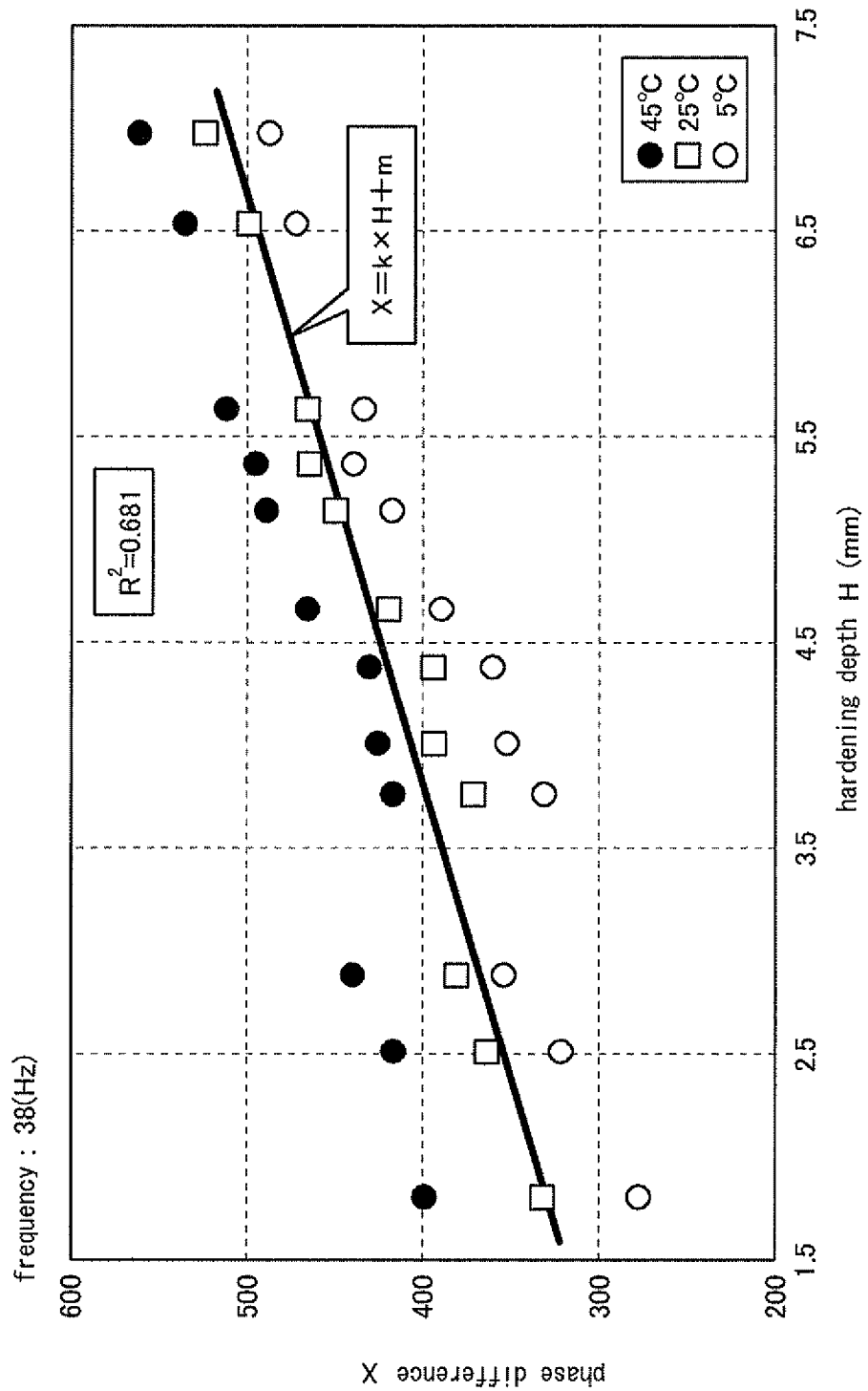
FIG. 9 is a diagram of relation between the phase difference X and the hardening depth H.

FIG. 9 is a graph of relation between the phase difference X at every measurement portion and the hardening depth H of the measurement object 102 in the case that the environment temperature is 5° C., 25° C. and 45° C. The graph shows that the phase difference X changes widely by change of the temperature and that, when the relation between the phase difference X and the hardening depth H is approximated to a linear function, the correlation is low ($R^2=0.681$), whereby the calculation of the hardening depth H with the linear function leads large measurement error caused by the change of environment temperature.

In the judgment process S6400, the hardening depth H calculated in the hardening depth calculation process S6300 is compared with a permissive hardening depth range set previously. When the hardening depth H is within the permissive hardening depth range, the measurement object 102 is judged to be a conforming article about the hardening depth. When the hardening depth H is out of the permissive hardening depth range, the measurement object 102 is judged to be a nonconforming article about the hardening depth.

The "permissive hardening depth range" indicates the range which is permissible as the hardening depth of the measurement object.

The sentence that "the hardening depth is within the permissive hardening depth range" indicates that the hardening depth is not less than the lower limit of the permissive hardening depth range and not more than the upper limit of the permissive hardening depth range.

The sentence that "the hardening depth is out of the permissive hardening depth range" indicates that the hardening depth is less than the lower limit of the permissive hardening depth range or more than the upper limit of the permissive hardening depth range.

In the judgment process S6400, the judgment part 131*e* compares the hardening depth H calculated by the hardening depth calculation part 131*d* with the lower limit and the upper limit of the permissive hardening depth range stored in the storage part 131*a*.

As the result of the comparison, when the hardening depth H is within the permissive hardening depth range, the judgment part 131*e* judges that the measurement object 102 is a conforming article about the hardening depth.

As the result of the comparison, when the hardening depth H is out of the permissive hardening depth range, the judgment part 131*e* judges that the measurement object 102 is a nonconforming article about the hardening depth. The judgment result of the measurement object 102 by the judgment part 131*e* is stored in the storage part 131*a* suitably.

As mentioned above, the embodiment of the hardening depth measurement method according to the present invention includes: the magnetization and detection process S6100 that the magnetization coil 111 applies the alternating current magnetization signals of the first frequency (in this embodiment, the frequency Fb) and the second frequency (in this embodiment, the frequency Fj) different from the first frequency on the measurement object 102 so as to generate the induced currents including the eddy currents respectively corresponding to the first frequency and the second frequency in the measurement object 102, and the detection coil 121 detects the detection signals caused by the induced currents respectively corresponding to the first frequency and the second frequency; the difference calculation process S6200 that the phase difference D shown in the formula 1 is calculated based on the amplitude Y1 of the detection signal corresponding to the first frequency (the frequency Fb), the phase difference X1 of the alternating current magnetization signal and the detection signal corresponding to the first frequency, the amplitude Y2 of the detection signal corresponding to the second frequency (the frequency Fj), and the phase difference X2 between the alternating current magnetization signal and the detection signal corresponding to the second frequency; and the hardening depth calculation process S6300 that the difference D calculated in the difference calculation process S6200 is substituted for the relational expression of the difference D, the hardening depth H of the measurement object 102, and the constants A and B shown in the formula 2 so as to calculate the hardening depth H of the measurement object 102.

According to the construction, the hardening depth H of the measurement object 102 can be measured with high accuracy noncontactly (nondestructively).

The invention claimed is:

1. A frequency selection method of eddy current measurement, wherein
a magnetization coil applies alternating current magnetization signals of a first frequency and a second frequency different from the first frequency on an measurement object so as to generate induced currents including eddy currents respectively corresponding to the first frequency and the second frequency in the measurement object,
a detection coil detects detection signals caused by the induced currents respectively corresponding to the first frequency and the second frequency,
a phase difference D shown in below formula 1 is calculated based on an amplitude Y1 of the detection signal corresponding to the first frequency, a phase difference X1 of the alternating current magnetization signal and the detection signal corresponding to the first frequency, an amplitude Y2 of the detection signal corresponding to the second frequency, and a phase difference X2 between the alternating current magnetization signal and the detection signal corresponding to the second frequency, and
the measurement object (the hardening depth thereof) is measured based on the phase difference D,
the method comprising:
a results of the magnetization and detection process for frequency selection that the magnetization coil applies alternating current magnetization signals of three or more different frequencies on the measurement object so as to generate induced currents respectively corresponding to the three or more different frequencies in the measurement object and the detection coil detects the detection signals caused by the induced currents respectively corresponding to the three or more different frequencies;
a phase difference calculation process that phase differences between the alternating current magnetization signals and the detection signals respectively corresponding to the three or more different frequencies are calculated based on the detection signals caused by the induced currents respectively corresponding to the three or more different frequencies detected in the magnetization and detection process for frequency selection; and
a frequency sampling process that a combination of two frequencies which make a difference of the phase differences within a predetermined range is extracted from the three or more different frequencies calculated in the phase difference calculation process, and lower one of the two frequencies of the combination is referred to as the first frequency and higher one thereof is referred to as the second frequency $$D = \frac{\sqrt{X_1^2 + Y_1^2} - \sqrt{X_2^2 + Y_2^2}}{\sqrt{X_2^2 + Y_2^2}}.$$ [Formula 1]

2. The frequency selection method according to claim 1, wherein the phase difference D is substituted for a relational expression of the difference D, a hardening depth H of the measurement object, and constants A and B shown in below formula 2 so as to calculate the hardening depth H of the measurement object.

$$D = A \times H^3 + B$$ [Formula 2]

3. A hardening depth measurement method comprising:
a magnetization and detection process that a magnetization coil applies alternating current magnetization signals of a first frequency and a second frequency different from the first frequency on a measurement object so as to generate induced currents including eddy currents respectively corresponding to the first frequency and the second frequency in the measurement object, and a detection coil detects detection signals caused by the induced currents respectively corresponding to the first frequency and the second frequency;
a difference calculation process that a phase difference D shown in below formula 1 is calculated based on an amplitude Y1 of the detection signal corresponding to the first frequency, a phase difference X1 of the alternating current magnetization signal and the detection signal corresponding to the first frequency, an amplitude Y2 of the detection signal corresponding to the second frequency, and a phase difference X2 between the alternating current magnetization signal and the detection signal corresponding to the second frequency; and
a hardening depth calculation process that the difference D calculated in the difference calculation process is substituted for a relational expression of the difference D, a hardening depth H of the measurement object, and constants A and B shown in below formula 2 so as to calculate the hardening depth H of the measurement object.

$$D = \frac{\sqrt{X_1^2 + Y_1^2} - \sqrt{X_2^2 + Y_2^2}}{\sqrt{X_2^2 + Y_2^2}}$$ [Formula 1]

$$D = A \times H^3 + B.$$ [Formula 2]

* * * * *

UNITED STATES PATENT AND TRADEMARK OFFICE
CERTIFICATE OF CORRECTION

PATENT NO. : 8,432,161 B2
APPLICATION NO. : 12/810875
DATED : April 30, 2013
INVENTOR(S) : Takanari Yamamoto Page 1 of 1

It is certified that error appears in the above-identified patent and that said Letters Patent is hereby corrected as shown below:

Title Page, delete in Item (56) under FOREIGN PATENT DOCUMENTS, Japanese Reference "A-2004-108573" to be replaced with "A-2004-108873".

Signed and Sealed this
Thirtieth Day of July, 2013

Teresa Stanek Rea
*Acting Director of the United States Patent and Trademark Office*